United States Patent [19]

Fink

[11] Patent Number: 4,661,107
[45] Date of Patent: Apr. 28, 1987

[54] HEART VALVE

[76] Inventor: Irving E. Fink, Box 1053, Fort Scott, Kans. 66701

[21] Appl. No.: 887,823

[22] Filed: Jul. 21, 1986

[51] Int. Cl.⁴ .............................................. A61F 2/24
[52] U.S. Cl. .................................. 623/2; 128/419 PS
[58] Field of Search ................ 137/554; 623/2, 24–26; 128/419 PS

[56] References Cited

U.S. PATENT DOCUMENTS

| | | | |
|---|---|---|---|
| 3,451,067 | 6/1969 | Jordan | 623/2 |
| 3,563,245 | 2/1971 | McLean | 128/419 PS |
| 3,696,674 | 10/1972 | Spencer | 623/2 |
| 3,932,898 | 1/1974 | Wright | 623/2 |
| 3,959,827 | 7/1974 | Kaster | 623/2 |
| 4,245,358 | 1/1981 | Moasser | 623/2 |

OTHER PUBLICATIONS

"Biologically-Energized Cardiac Pacemakers", by Myers et al, *The American Journal of Medical Electronics*, Oct.-Dec. 1964.

"A Cardiac Pacemaker Using Biologic Energy Sources", by Parsonnet et al., vol. 9, *Frans. Amer. Society for Artificial Organs.*

"Intracardiac Pressure Changes Utilized to Energize a Piezoelectric Powered Cardiac Pacemaker", by Staueh et al, *Ibid*, vol. 16.

*Primary Examiner*—Richard J. Apley
*Assistant Examiner*—James Prizant
*Attorney, Agent, or Firm*—Mark C. Jacobs

[57] ABSTRACT

A pacemaker battery charging system that utilizes the pumping action of a modified heart valve to recharge the battery of the pacemaker by creating a current inductance as the valve operates, which current is supplied to the pacemaker's rechargeable battery.

7 Claims, 7 Drawing Figures

HEART VALVE

BACKGROUND OF THE INVENTION

Pacemakers are well known and are available in the marketplace from such vendors as General Electric and Medtronics. These devices are powered by long but finite life batteries, such as lithium cells. Sometimes these cells fail early in their life. When the battery wears out, either early, or after a period of usage, it becomes necessary to make an incision in the body to replace the battery. This surgical procedure, like any surgical procedure should be avoided, if possible.

It is an object therefore to provide in this invention a battery recharging system useful with nickel cadmium and other rechargeable batteries that can or could be employed with a pacemaker.

It is another object to provide a heart valve capable of setting up an inductance.

It is a further object to provide a battery charging system that utilizes an inducted current generated from a heart valve to charge a pacemaker battery.

Other objects of the invention will in part be obvious and will in part appear hereinafter.

The invention accordingly comprises the apparatus possessing the construction, combination of elements and arrangement of parts which are exemplified in the following detailed disclosure, and the size of the application of which will be indicated in the claims.

For a fuller understanding of the nature and objects of the invention, reference should be had to the following detailed description taken in connection with the accompanying drawings.

SUMMARY OF THE INVENTION

A heart valve of any design that provides for the movement of a valve element partially into an annulus can be modified to produce an inductance current, which current can be used by the other components of the charging system of this invention to charge a rechargeable battery for a pacemaker.

DESCRIPTION OF THE PREFERRED EMBODIMENT

Pacemakers and the recharging of a battery system for pacemakers forms the subject matter of this invention. However since pacemakers are such well known articles of commerce in this day and age, it is not within the scope of this invention to discuss the use and operation of a pacemaker, for such is well known.

Battery recharging systems are also well known, as are various modes of encapsulating pieces of hardware such as a recharger to render it inert to body chemistry. As such the discussion herein will be limited to the provision of a new heart valve and/or the modification of suitable prior art valves to provide a source of current for state of the art battery rechargers.

Figure 1:
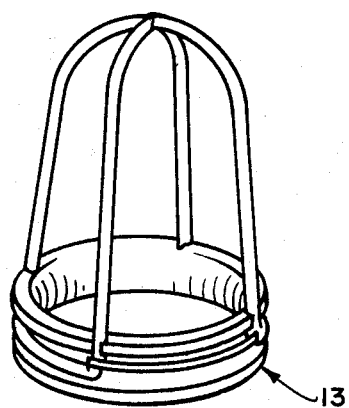
FIG. 1 is a perspective view of a typical heart valve cage but without the valve element, of the prior art which valve cage can be modified to be operable in this invention.

Turning now to FIG. 1, the prior art heart valve cage shown here is the valve disclosed and claimed in the Wright U.S. Pat. No. 3,932,898 issued Jan. 20, 1976. The manufacture of that valve is fully recited in that patent, and the specification of which is incorporated herein by reference. While not shown in the patent it is readily understood, that such a valve employs a spherical element that moves within the confines of the cage from the apex thereof, down to the opening within the annular ring.

Figure 2:
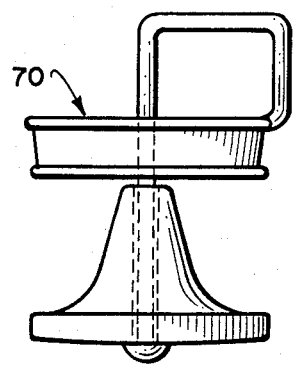
FIG. 2 is a perspective view of a second prior art heart valve that can be modified for use in this invention.

FIG. 2 depicts the prir art heart valve disclosed and claimed in the Jorden U.S. Pat. No. 3,451,067, issued June 24, 1969. The mode of production of that device is fully recited therein, and the specification concerning same is incorporated herein by reference into this application. This valve employs the valve element shown in the Figures, and that entire valve may be employed herein, after modification, among others, as will be discussed below.

The common feature of both of the valves is the annular member or ring which in the Jorden patent is designated 70 and in the Wright patent is designated the base member 13. This annular member serves as the fundamental member for this invention.

Figure 3:
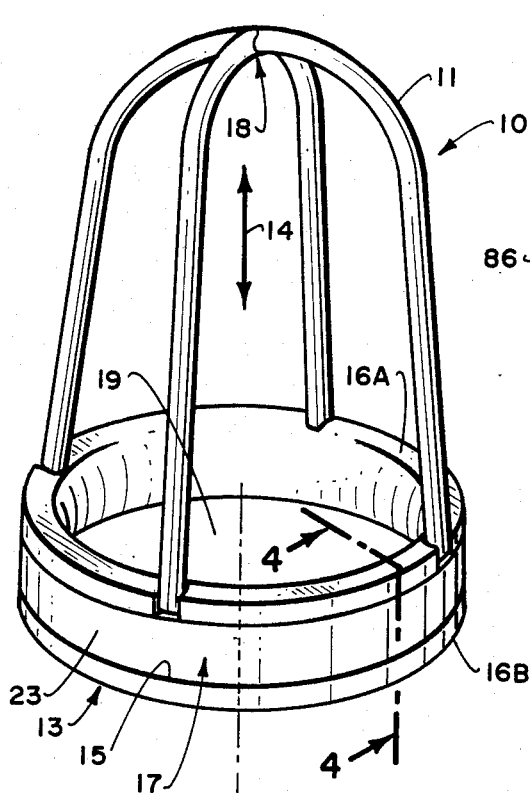
FIG. 3 is a perspective view of a suitable modified version of the heart valve of FIG. 1 for use in the system of this invention.

Reference is now made to FIG. 3 wherein the modified heart valve 10, of this invention is shown. Here the modified valve designated 10, includes a cage 11, an annular base member 13, attached to said cage, and a valve element usually in the shape of a sphere 12 which moves upwardly in the direction of arrow 14 within the cage from apex 18 down to the opening 19 within the annular ring 13, as is known in the art, through which cage flows blood when the valve is open. Annular base 13 includes an upstream outward extending circular ridge 16A, and a downstream outward extending circular ridge 16B.

An encapsulated coil of wire 17 is seen disposed in or on the recess 15.

Figure 4:
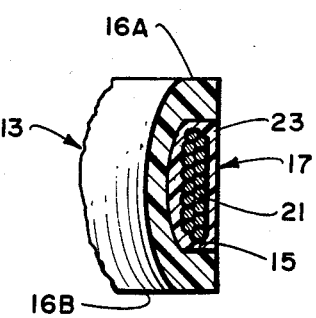
FIG. 4 is a sectional view taken along line 4—4 of FIG. 3.

Attention of the reader is now turned to FIG. 4, a sectional view taken along the line 4—4 of FIG. 3. Here encapsulated coil 17 is seen to include a plurality of wire windings 21 of any suitable uninsulated copper wire, encapsulated in a plastic jacket 23.

It is within the skill of the art to determine the number of windings needed and the gauge of the wire necessary to satisfy the requirements of this invention. Suitable encapsulation materials could include polycarbonate, polyester, nylon or other materials inert with respect to body chemistry.

The two leads 21 and 23 from the coil 17 are connected to the balance of the recharging system as will be discussed below.

In order to set up an inductance,, a two poled magnetic element must be moved through the coil 17. This is a well known principle of electronics. In the case at hand, the magnetic two poled element is either in the form of a disk, not shown, or a sphere which moves within the cage 11 down to the base 13, thus closing off the opening 19 within the base member 13. This stops the flow of blood, which flow can recommence on the exit or out stroke, i.e. movement of the valve element up and away from the opening 19. The poles are designated 25 and 27, while the balance of the magnet is designated 26. The magnet is shown in dotted line as it is buried within the spherical valve element.

Figure 5:
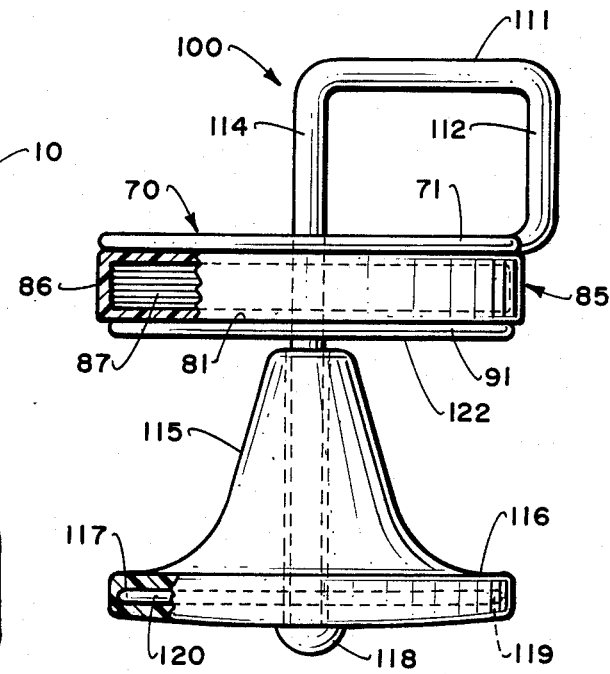
FIG. 5 is a perspective view of a second modified valve for use herein.

A second valve that can be modified to be used in accordance with this invention is the one of Jordan, seen in FIG. 2. This modified valve designated 100 is seen in FIG. 5. It features a bell shaped valve element 115 seen in that figure. The valve element moves on the vertical section 114 of the wire frame 111. The annular ring 70 is retained by segment 112 of the wire frame. Ring 70 includes an upstream lip 71 and a downstream lip 91 with a recess 81 upon which is formed the coil 85. Coil 85 is formed in like manner as the coil described with respect to FIG. 4. Here the two leads are designated 86 and 87.

The valve element 115 has a lower circular portion 116 which includes a magnet 120 buried therein, which magnet has a north pole 117 and a south pole 119. Designator 118 limits the downward travel of the valve element.

In both embodiments a strip magnet is placed in the valve element such that one pole is at one end and the other pole at the second end of the valve element. This placement is most easily accomplished if the valve element, which is usually of inert plastic is formed, i.e. molded around the magnet.

Optionally in accordance with the teachings of the Jordan patent, ridge 122 may have a convex surface to aid in the seating of the valve element.

Figure 6:
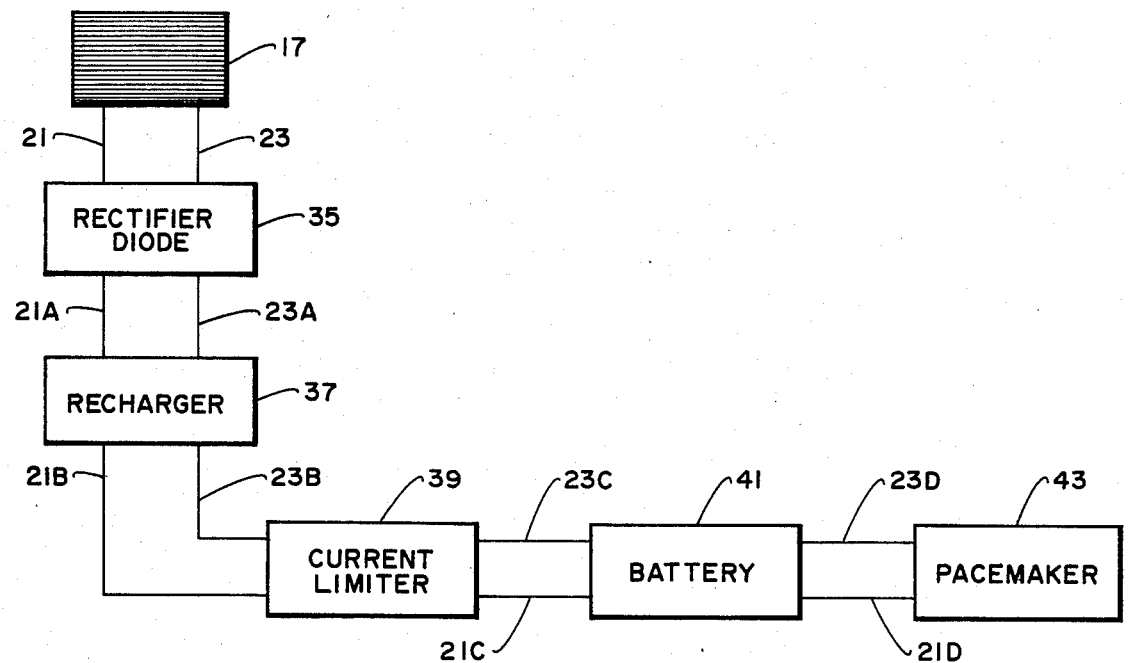
FIG. 6 is a black box diagram illustrating the charging system of this invention.

Reference is now made to FIG. 6 which shows in graphic form the charging system of this invention. Leads 21 and 23 from the encapsulated wire coil are electrically connected to the diode rectifies 35.

The diode rectifier 35 converts the AC current from the inductance to DC current. DC current then flows from the rectifier 35 through leads 21A, 23A, to the battery recharger 37 since these are electrically connected to each other.

Optionally but preferably connected to the output of the charger 37, by leads 21B, 23B is a current limiter 39. Such devices 39 are well known in the art and are used to prevent overcharging of the battery 41. The battery 41, is electrically connected to the recharger 37, directly or via the interposed current limiter, by leads 21C, 23C. The battery is of course electrically connected to the pacemaker's circuitry 43 by leads 21D, 23D.

Figure 7:
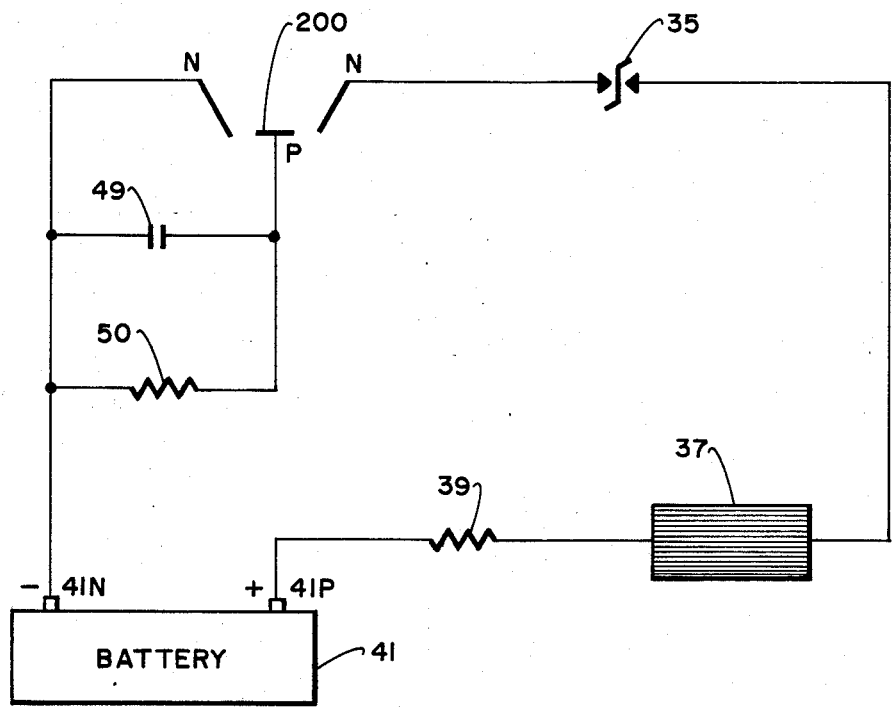
FIG. 7 is an electrical schematic diagram of a charging system according to this invention wherein a current limiting device is employed.

A typical current limiting device 37 for incorporation in this circuit is shown diagrammatically in FIG. 7. Current flow in FIG. 7 is from the battery 41's negative terminal 41N through transistor 200 of current limiter 39, through diode rectifier 35 to battery charger 37. The current then passes through current limiting resistor 39 terminating at the position terminal 41P of battery 41.

Transistor 200 conducts current when the base of the PNP device is at a negative potential in relation to the transistor's collector and emitter. Current stops when the positive potential of the batter's positive terminal 41P through resistor C50 produces a positive potential at the base of the PNP transistor, 200. This is turn aids the cooling of the wire coil 17, in valve 10, which valve is cooled by the passage of blood through the heart valve while current is flowing.

Note that both of the coil and the balance of the valve are cooled by the termination of current flow and blood passage.

It is seen that during the operation of the artificial heart valve, of the first embodiment, the magnet in the valve element moves from within the cage, to a position within the annular ring, to thereby prevent the flow of blood. The full operation of the artificial heart valve is beyond the scope of this invention and need not be discussed at length.

As the valve element moves to close the opening, an induction is set up. This AC current is converted to DC by the diode rectifier 35; passes to the recharger 37 and from there optionally via the interposed current limiter 39 to the pacer 43's battery 41. The operation of the modified Jordan valve works on the same principle. The presence of the moving magnet within the coil sets up an inductance which is used by the balance of the circuit.

Since each component is separately known and available in the marketplace, further details need not be spelled out on any particular component.

In operation as the AC current is generated by inductance, it is rectified to DC and passed to the charger which will charge the battery of the pacer, which is electrically connected thereto. A typical battery that can be recharged is a nickel-cadmium battery. However other chemical rechargeable batteries are known in the art and can be similarly recharged.

To make the special valve housing of this invention, for use in the first embodiment,—since the reference numbers cited next refer thereto, though the concept is equally applicable to the second embodiment—the coil 17 can be wound in place and the base member 13 dipped into a suitable encapsulation material, or the encapsulation material can be molded around the coil. It may also be possible to form a prewound encapsulated coil and snap it onto the base member's annular recess.

The modified valve element for the use in the valve housing would be formed by any known mode, including but limited to moulding the element around a magnet.

While the instant invention has been illustrated using two different artificial heart valves as the source of an inducted current it is to be seen that any valve housing having an annular base upon which an electrical wire coil can be disposed may be used with any valve element into which can be placed a magnet. It is within the skill of the art to match a valve element with a valve housing to create the needed induction for use in the battery charging system of this invention.

As is known the blood circulation system is a closed loop. The heart functions as a positive displacement pump with the various valves, both natural and artificial employed to permit unidirectional flow. In general the opening and closing of the several valves is by the velocity of the blood flow.

It is beyond the scope of this patent to discuss the implementation of the instant valve into the heart. Such is readily within the skill of those doctors who practice such art.

Pacemakers are also well known and such means need not be discussed at length within the scope of this application.

While the charging system of this invention is most applicable for use with a heart pacemaker, it is readily seen that its use is equally applicable with such other medical devices, as muscle stimulators e.g. devices to aid in the flexing of the knee to facilitate walking, among others.

Since certain changes may be made in the above apparatus without departing from the scope of the invention herein involved, it is intended that all matter contrary to the above description shall be interpreted as illustrative and not in a limiting sense.

I claim:

1. An artificial heart valve composed of materials which are inert to the human body and which is capable of creating an electrical inductance which comprises:
   a. a valve housing having an annular base with a coil of wire encapsulated in a suitable plastic disposed around the perimeter of the annular base, said base having an opening therein,
   b. a pair of electrical leads emanating from said coil for attachment to an electrical circuit,
   c. a valve element having a magnet disposed therein, said element having a north pole and a south pole, said valve element adapted for movement within the valve housing whereby on the movement of said element from a distant position to a proximal position, the element closes off the opening in said annular base, thereby causing a current to be induced.

2. The artificial heart valve of claim 1 wherein the valve element is bell shaped.

3. The artificial heart valve of claim 1 wherein the valve element is spherical.

4. The artificial heart valve of claim 1 wherein the encapsulated material is selected from the group consisting of polycarbonate, nylon and polytetrafluoroethylene.

5. A pacemaker rechargeable battery charging system comprising in combination:
   a. a heart valve comprising an occluder element which contains a magnet and is capable of providing an inducted AC current,
   b. a diode rectifier electrically connected to said valve,
   c. a battery charger electrically connected to said diode rectifier and,
   d. a rechargeable battery adapted for use in a pacemaker, electrically connected to said battery charger.

6. The pacemaker battery recharging system of claim 5 further including a current limiting means interposed in system's circuitry.

7. The pacemaker battery recharging system of claim 5 wherein the artificial heart valve capable of providing an induced current includes a valve housing having an annular base around which is disposed an encapsulated wire coil from which emanates a pair of leads and a central opening and a valve element having a magnet therein, said element adapted cooperate with said valve element whereby on closing of the opening in said valve housing a current is induced.

* * * * *